United States Patent
Beck et al.

(10) Patent No.: US 10,762,356 B2
(45) Date of Patent: Sep. 1, 2020

(54) METHOD AND SYSTEM FOR GENERATING AN OUTPUT WITH RESPECT TO A GROUP OF INDIVIDUALS

(71) Applicant: PANASONIC INTELLECTUAL PROPERTY MANAGEMENT CO., LTD., Osaka (JP)

(72) Inventors: Ariel Beck, Singapore (SG); Khai Jun Kek, Batu Pahat (SG); Vasileios Vonikakis, Singapore (SG); Chandra Suwandi Wijaya, Singapore (SG)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 74 days.

(21) Appl. No.: 15/984,963

(22) Filed: May 21, 2018

(65) Prior Publication Data
US 2019/0354777 A1    Nov. 21, 2019

(51) Int. Cl.
*G06K 9/00* (2006.01)
*G06F 3/01* (2006.01)
*G06Q 30/02* (2012.01)

(52) U.S. Cl.
CPC .......... *G06K 9/00778* (2013.01); *G06F 3/011* (2013.01); *G06K 9/00268* (2013.01); *G06K 9/00342* (2013.01); *G06Q 30/0251* (2013.01); *G06F 2203/011* (2013.01)

(58) Field of Classification Search
CPC .................................................. G06K 9/00778
USPC ......................................................... 382/118
See application file for complete search history.

(56) References Cited

U.S. PATENT DOCUMENTS

| 8,195,598 B2 | 6/2012 | Hua et al. |
| 2005/0096084 A1* | 5/2005 | Pohja ................. G06Q 10/10 455/556.1 |
| 2011/0058028 A1* | 3/2011 | Sakai ................. G06K 9/00288 348/77 |
| 2011/0309946 A1* | 12/2011 | Jonsson ............. H04M 1/72563 340/686.6 |
| 2012/0265495 A1* | 10/2012 | Aimin ................. G01S 17/023 703/1 |
| 2016/0350801 A1 | 12/2016 | Vincent et al. |

(Continued)

FOREIGN PATENT DOCUMENTS

WO    2016/195474 A1    12/2016

*Primary Examiner* — Stephen P Coleman
(74) *Attorney, Agent, or Firm* — McDermott Will & Emery LLP

(57) ABSTRACT

There is provided a computer-implemented method for generating an output with respect to a group of individuals. The method includes: identifying the group of individuals amongst a plurality of individuals in an area being monitored by one or more sensors; determining, for each individual in the group of individuals, one or more individual-based features associated with the individual based on sensing data obtained from the one or more sensors; determining a group characteristic information associated with the group of individuals based on the one or more individual-based features determined for each individual in the group; and generating the output based on the group characteristic information determined for the group of individuals. There is also provide a corresponding system for generating an output with respect to a group of individuals.

26 Claims, 12 Drawing Sheets

(56) References Cited

U.S. PATENT DOCUMENTS

2017/0105662 A1    4/2017   Silawan et al.
2017/0178345 A1*  6/2017   Pham ................. G06K 9/00771

* cited by examiner

METHOD AND SYSTEM FOR GENERATING AN OUTPUT WITH RESPECT TO A GROUP OF INDIVIDUALS

TECHNICAL FIELD

The present invention generally relates to a computer-implemented method for generating an output with respect to a group of individuals and a system thereof, such as but not limited to, targeted information (e.g., a targeted advertisement content).

BACKGROUND

In a wide variety of applications, it may be desirable to generate an output (e.g., provide or present targeted information, such as a targeted advertisement content) with respect to various individuals detected by a sensor. For example, a conventional system may be configured to determine a feature, such as a characteristic or an attribute, associated with an individual and then output a targeted advertisement content based on the feature of the individual determined. For example, if the individual is detected to be young, then a targeted advertisement content targeting young people may be provided. On the other hand, if the individual is detected to be old, then a targeted advertisement content targeting elder people may be provided instead.

However, such conventional systems of providing targeted information may only be capable of targeting information directly in accordance with one or more basic types of features detected, such as gender, age, emotional state, and so on, of a single individual, and thus, the categories of information which may be targeted may be undesirably limited or restricted. For example, conventional systems may only be able to provide targeted information to an individual directly in accordance to the individual's gender, age, and/or emotional state detected.

A need therefore exists to provide a method for generating an output, such as but not limited to, targeted information (e.g., a targeted advertisement content), and a system thereof, that seek to overcome, or at least ameliorate, one or more of the deficiencies of conventional methods and systems, such as the conventional methods and systems as mentioned above. It is against this background that the present invention has been developed.

SUMMARY

According to a first aspect of the present invention, there is provided a computer-implemented method for generating an output with respect to a group of individuals, the method comprising:

identifying the group of individuals amongst a plurality of individuals in an area being monitored by one or more sensors;

determining, for each individual in the group of individuals, one or more individual-based features associated with the individual based on sensing data obtained from the one or more sensors;

determining a group characteristic information associated with the group of individuals based on the one or more individual-based features determined for each individual in the group; and generating the output based on the group characteristic information determined for the group of individuals.

According to a second aspect of the present invention, there is provided a system for generating an output with respect to a group of individuals, the system comprising:

a memory;

at least one processor communicatively coupled to the memory and configured to:

identify the group of individuals amongst a plurality of individuals in an area being monitored by one or more sensors;

determine, for each individual in the group of individuals, one or more individual-based features associated with the individual based on sensing data obtained from the one or more sensors;

determine a group characteristic information associated with the group of individuals based on the one or more individual-based features determined for each individual in the group; and generate the output based on the group characteristic information determined for the group of individuals.

According to a third aspect of the present invention, there is provided a computer program product, embodied in one or more non-transitory computer-readable storage mediums, comprising instructions executable by at least one processor to perform a method for generating an output with respect to a group of individuals, the method comprising:

identifying the group of individuals amongst a plurality of individuals in an area being monitored by one or more sensors;

determining, for each individual in the group of individuals, one or more individual-based features associated with the individual based on sensing data obtained from the one or more sensors;

determining a group characteristic information associated with the group of individuals based on the one or more individual-based features determined for each individual in the group; and generating the output based on the group characteristic information determined for the group of individuals.

BRIEF DESCRIPTION OF THE DRAWINGS

Embodiments of the present invention will be better understood and readily apparent to one of ordinary skill in the art from the following written description, by way of examples only, and in conjunction with the drawings, in which.

DETAILED DESCRIPTION

As described in the background, in a wide variety of applications, it may be desirable to generate an output (e.g., provide or present targeted information, such as a targeted advertisement content) with respect to various individuals detected by a sensor. For example, a conventional system may be configured to determine a feature, such as a characteristic or an attribute, associated with an individual and then output a targeted advertisement content based on the feature of the individual determined. However, such conventional systems of providing targeted information may only be capable of targeting information directly in accordance with one or more basic types of features detected, such as gender, age, emotional state, and so on, of a single individual, and thus, the categories of information which may be targeted may be undesirably limited or restricted.

For example, conventional approaches in "smart" advertisement may focus solely on individual-based features, such as age group (e.g., targeted advertisement based on the age of an individual), gender (e.g., targeted advertisement based on the gender of the individual, for example, male and female may not be interested in the same items), clothing (e.g., targeted advertisement based on the attire or style of an individual, for example, in the interest of recommending related shops or brands), emotional state (e.g., targeted advertisement based on the mood of an individual). However, such conventional approaches are at an individual level only in the sense that they are only capable of providing targeted information directly in accordance with one or more basic types of features detected of a single individual. For example, it has been identified according to various embodiments of the present invention that no information about the context associated with the individual is obtained in such conventional approaches, such as, whether the individual is present with his/her family as a group, whether the individual is present with his/her partner as a group, and so on. Therefore, such conventional approaches are not capable of providing information on multiple individuals considered as a group. As a result, such conventional approaches are not able to, for example, provide targeted advertisement content that are applicable to a group of individuals (i.e., at a group level).

Various embodiments of the present invention provide a computer-implemented method for generating an output, and a system thereof, that seek to overcome, or at least ameliorate, one or more of the deficiencies of conventional methods and systems, such as the conventional methods and systems as mentioned in the background. In particular, various embodiments of the present invention provide a computer-implemented method for generating an output with respect to a group (or a set) of individuals, and a system thereof.

Figure 1:
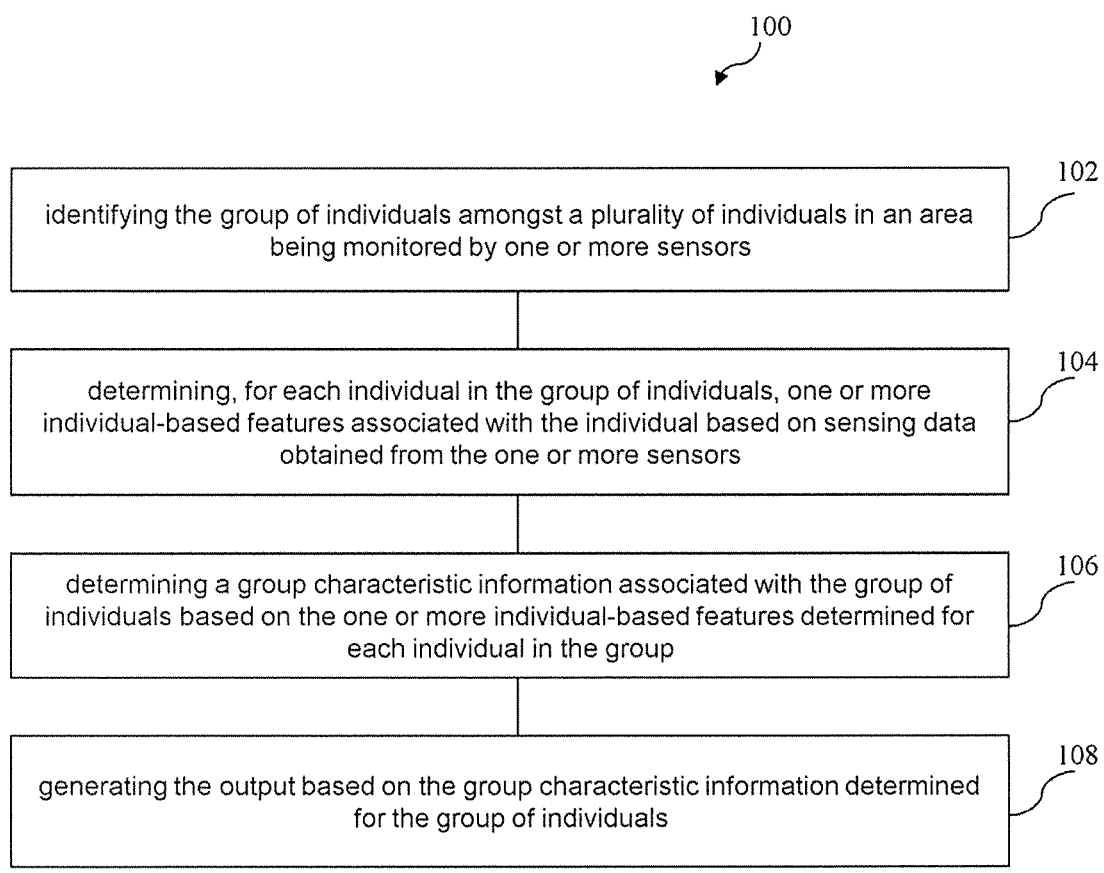
FIG. 1 depicts a schematic flow diagram of a method for generating an output with respect to a group of individuals according to various embodiments of the present invention.

FIG. 1 depicts a schematic flow diagram of a method 100 (computer-implemented method) for generating an output with respect to a group of individuals (which may also be referred to as subjects or persons). The method 100 comprises a step 102 of identifying the group of individuals amongst a plurality of individuals in an area being monitored by one or more sensors; a step 104 of determining, for each individual in the group of individuals, one or more individual-based features associated with the individual based on sensing data obtained from the one or more sensors; a step 106 of determining a group characteristic information associated with the group of individuals based on the one or more individual-based features determined for each individual in the group; and a step 108 of generating the output based on the group characteristic information determined for the group of individuals. In the context of various embodiments, it will be understood by a person skilled in the art that the term "individual" may refer to an individual person. It will also be understood by a person skilled in the art that the term "individual-based feature" (which may also be interchangeably referred to as "individual-associated feature") may refer to any feature associated with an individual (i.e., at an individual level or with respect to the individual), such as a characteristic or an attribute, of the individual.

In relation to step 102, for example, one or more groups of individuals may be identified in an area being monitored. That is, one or more individuals amongst the plurality of individuals may be determined to belong (or relate) as one group (i.e., same group) and may thus be assigned to one particular group. In this manner, one or more separate groups of individuals, each comprising one or more individuals determined to belong to the respective group, may thus be identified in an area being monitored. In this regard, since the method 100 is configured to identify a group of individuals, the method 100 is advantageously able to generate an output with respect to the group of individuals identified (i.e., at a group level), for example, instead of merely with respect to a single individual detected (i.e., at an individual level only). As a result, for example, the method 100 advantageously broadens the categories of information which may be targeted, thus enabling more appropriate/relevant or better suited information to be provided or presented to the group of individuals, for example, taking into account one or more features at a group level instead of at an individual level. For example, the categories of information are no longer limited or restricted to one or more basic types of features associated with a single individual detected, such as gender, age, emotional state, and so on, but are broadened to be able to accommodate for characteristics (e.g., relationship, context and so on) associated with a group of individuals detected (group characteristic information), such as but not limited to, a couple, a family, a group of colleagues, and so on.

By way of examples only and without limitation, in the case of a couple (group characteristic information) being detected as a group, a targeted advertisement for a romantic holiday for two or a romantic dinner for two may be provided, and in the case of a family (group characteristic information) being detected as a group, a targeted advertisement for a family holiday with a stay in a villa or a trip to the zoo may be provided. Such categorizations or classifications of information are not possible with conventional techniques that only take into account one or more features associated with one individual (i.e., at an individual level). For example, although a middle age man may be detected, such convention techniques are not able to determine whether such a middle age man is present as a couple or as a family. Therefore, according to embodiments of the present invention, categories of information which may be targeted are advantageously broadened, thus enabling more appropriate/relevant or better suited information to be provided or presented to the group of individuals.

In relation to step 104, for example, for a group of individuals that has been identified, one or more features (individual-based features) associated with each individual in the group may then be determined based on sensing data obtained from the one or more sensors. It can be appreciated by a person skilled in the art that the presented invention is not limited to any particular types of features associated with an individual that can be determined, as long as the feature(s) associated with the individual may be used for, or may facilitate in, categorizing or classifying purposes with respect to the individual.

In various embodiments, the one or more individual-based features determined may preferably be selected from the group consisting of facial feature(s), body feature(s), spatial feature(s) (e.g., position/location of an individual, such as coordinates), and speech feature(s). It can be understood by a person skilled in the art that each type of these individual-based features may be determined by a corresponding classifier or analysis module, such as a facial feature classifier configured to determine one or more facial features, a body feature classifier configured to determine one or more body features, a spatial feature classifier configured to determine one or more spatial features, and a speech feature classifier configured to determine one or more speech features, based on the sensing data obtained from one or more sensors.

In various embodiments, the one or more sensors are selected from the group consisting of a motion sensing device, a range sensing device (e.g., a time-of-flight (ToF) sensing device), an image capturing device, and an audio capturing device.

In relation to step 106, based on the one or more individual-based features determined for each individual in the group, a group characteristic information for the group may subsequently be determined. In the context of various embodiments, the group characteristic information indicates one or more characteristics determined for the group of individuals as a whole (i.e., at a group level). By way of examples only and without limitations, the group characteristic information may indicate that the group is a couple, a family, happy, active, and so on. It will be appreciated by a person skilled in the art that the group characteristic information may indicate any number of characteristics as appropriate or as desired, such as a young couple or a happy family. In various embodiments, the group characteristic information may indicate a relationship amongst the individuals in the group (which may also be referred to as a group relationship information), for example, a couple or a family as mentioned hereinbefore. In this regard, it will be appreciated by a person skilled in the art that various classification techniques/algorithms may be applied for producing a classification result/output based on one or more inputs obtained/detected, and the present invention is limited to any particular type of classification technique/algorithm.

By way of examples only and without limitations, various classification techniques/algorithms include support vector machine (SVM), probabilistic neural network (PNN), and k-nearest neighbour (KNN), which are known in the art and thus need not be described herein. That is, it can be understood by a person skilled in the art that any appropriate classification technique known in the art may be applied to produce a classification result/output (group characteristic information) based on the one or more individual-based features determined for each individual in the group. By way of example, SVMs are supervised learning models with associated learning algorithms that analyze data for classification and regression analysis, and SMVs may build a model based on training data (e.g., training sets of one or a combination of types of features and the corresponding desired group characteristic information) for determining (e.g., predicting) the classification result/output based on inputs received (e.g., individual-based features determined for each individual in the group).

In relation to step 108, for example, the group characteristic information determined for the group of individuals may then be used to generate an output for various applications as desired or as appropriate. In various embodiments, the group characteristic information may be used to generate an output selected from the group consisting of a targeted advertisement content, a targeted security alert (e.g., an illegal or suspicious gathering of a group of individuals), an environment setting (e.g., a light setting and/or background music setting), and a signal or message comprising the group characteristic information. However, it will be appreciated to a person skilled in the art that the present invention is not limited to such applications and may be applied to generate an output for various other applications as desired or as appropriate, as long as the output is desired to be dependent or based on the group characteristic information associated with a group of individuals determined. For example, it will be appreciated by a person skilled in the art that the above-mentioned output may be a signal or message comprising the group characteristic information for transmission to one or more devices or systems configured for specific application(s) (e.g., for generating advertisement content, security alert or environment setting), such that the one or more devices or systems generate their output based on the signal or message received. In other words, it will be appreciated by a person skilled in the art that a device or system configured for specific application(s) may be further configured to perform the method 100 to generate an output in the form of a content, an alert or an effect based on the group characteristic information (e.g., an advertisement display system, such as a digital signal system, may be configured to produce/display an advertisement content based on the group characteristic information), or a device or system (e.g., may be referred to as a group characteristic information device or system) may be configured to perform the method 100 to generate an output in the form of a signal or message comprising the group characteristic information for transmission to one or more devices or systems configured for specific application(s), such that the one or more devices or systems generate their output based on the signal or message received. For example, the group characteristic information device or system may output a signal or message comprising the group characteristic information to an advertisement display system such that the advertisement display system generates/displays an advertisement content based on the group characteristic information in the signal or message received.

Accordingly, the method 100 according to various embodiments of the present invention advantageously broadens the categories of information (e.g., advertisement content or control signals (e.g., environment settings)) which may be targeted, thus enabling more appropriate or better suited information or control signals to be provided with respect to the group of individuals, for example, taking into account one or more features at a group level instead of at an individual level. For example, the method 100 according to various embodiments of the present invention is advantageously able to understand group dynamics/characteristics and enables the provision of information that effectively targets a group of individuals.

In various embodiments, the method 100 further comprises determining one or more group-based features associated with the group of individuals based on the one or more individual-based features determined for each individual in the group. In this regard, the group characteristic information may be determined based on the one or more group-based features determined for the group of individuals. Similarly, it will be understood by a person skilled in the art that the term "group-based feature" (which may also be interchangeably referred to as "group-associated feature") may refer to any feature associated with a group (i.e., at a group level or with respect to the group), such as a characteristic or an attribute, of the group. It will be appreciated by a person skilled in the art that the presented invention is not limited to any particular types of group-based features that can be determined, as long as the group-based feature(s) may be used for, or may facilitate in, categorizing or classifying purposes with respect to the group. By way of examples only and without limitations, the group-based features(s) may include proxemics-based feature(s) or characteristic(s) (e.g., degree of separation or the interpersonal distances of individuals in the group, for example, whether they are within an intimate space, a personal space, a social space or a public space), a shape or configuration of the group (e.g., the shape or configuration formed by the group), sound/voice features (e.g., voice patterns in the group or detecting voice barge-in), group synchrony or behavior (e.g., the synchrony of body movements of individuals in the group), group origin (e.g., the ethnicity of the majority of individuals in the group), and so on. It will be understood by a person skilled in the art that each type of group-based features may be determined by one or more corresponding classifier or analysis module based on various individual-based features determined. Furthermore, similarly as described hereinbefore, it will be appreciated by a person skilled in the art that various classification techniques/algorithms may be applied for producing a classification result/output based on one or more inputs (group-based features) obtained/detected, and the present invention is limited to any particular type of classification technique/algorithm. That is, it can be understood by a person skilled in the art that any appropriate classification technique known in the art may be applied to produce a classification result/output (group characteristic information) based on the one or more group-based features determined for the group of individuals. By way of example, SVMs are supervised learning models with associated learning algorithms that analyze data for classification and regression analysis, and SMVs may build a model based on training data (e.g., training sets of one or a combination of types of features and the corresponding desired group characteristic information) for determining (e.g., predicting) the classification result/output based on inputs received (e.g., group-based features determined for the group of individuals).

In various embodiments, the step 102 of identifying the group of individuals comprises a step of determining a separation between each adjacent pair of individuals (i.e., a separation between an adjacent pair of individuals for each adjacent pair of individuals) amongst the plurality of individuals; a step of determining an orientation of each individual of the plurality of individuals; and a step of determining, for each adjacent pair of individuals, whether to assign the adjacent pair of individuals as belonging to the group of individuals based on the separation determined with respect to the adjacent pair of individuals and the orientation determined with respect to each individual of the adjacent pair of individuals. For example, the separation may be derived from spatial features (e.g., positions/locations, such as coordinates) of the individuals. In various example embodiments, a pairwise distance may be determined between each adjacent pair of individuals and the separation between each adjacent pair of individuals may thus be indicated by or correspond to the pairwise distance determined.

In various embodiments, the step of determining whether to assign the adjacent pair of individuals comprises determining to assign the adjacent pair of individuals as belonging to the group on individuals if the separation between the adjacent pair of individuals determined satisfies a predetermined separation condition and the orientations of the adjacent pair of individuals determined satisfy a predetermined orientation condition.

In various embodiments, the predetermined separation condition is that the separation determined is less than a predetermined separation (e.g., a predetermined distance), and the predetermined orientation condition is that the orientations determined are toward each other. For example, various studies in the past have been conducted and a number of particular interpersonal distances have been concluded to represent various circumstances associated with an individual. For example, about 0 to 0.45 m may represent an intimate space, about 0.45 m to about 1.2 m may represent a personal space, about 1.2 m to about 3.6 m may represent a social space, and about 3.6 m to 7.6 m may represent a public space. Accordingly, the predetermined separation may be set as desired or as appropriate, for example, based on various studies conducted in the past, such as but not limited to, about 3.6 m. In various embodiments, the orientations of a pair of individuals may be determined to be toward each other as long as the direction vectors associated with the pair of individuals, respectively, are convergent, such as converging towards a point or intersects at a point.

For example, a first adjacent pair of individuals may be determined to belong as a group if they satisfy both the predetermined separation condition and the predetermined orientation condition, and thus may be assigned to the same group (e.g., first group). In addition, a second adjacent pair of individuals may also be determined to belong as a group if they satisfy both the predetermined separation condition and the predetermined orientation condition, and thus may be assigned to the same group (e.g., second group). Furthermore, there may be an individual common to both the first and second groups, and in such a case, the first and second groups may then be merged as one group.

In various embodiments, the step 102 of identifying the group of individuals further comprises generating a schematic model for each individual of the plurality of individuals. In this regard, the separation and the orientation are determined based on the schematic model of the respective individual.

In various embodiments, the schematic model is a skeleton model or a face model, and the separation is determined based on one or more predetermined first portions of the respective skeleton model or face model and the orientation is determined based on a direction vector generated based on one or more predetermined second portions of the respective skeleton model or face model. For example, in various example embodiments, in the case of a skeleton model, the first portion may correspond to the thorax portion of the skeleton model, and the second portions may correspond to the left and right shoulder end portions of the skeleton model. For example, the direction vector may be perpendicular to a line (e.g., from a center of the line) joining/connecting the left and right shoulder end portions of the skeleton model. For example, in various example embodiments, in the case of a face model, the first portion may correspond to a central portion (e.g., nose portion) of the face model, and the second portions may correspond to the left and right eye portions (or ear portions) of the face model. Similarly, the direction vector may then be perpendicular to a line (e.g., from a center of the line) joining/connecting the left and right eye portions (or ear portions) of the face model. It will be appreciated to a person skilled in the art that various other types of schematic models may be used to model or represent an individual as desired or as appropriate, as long as the position and orientation of the individual can be derived from the schematic model.

In various embodiments, the step 104 of determining one or more individual-based features comprises determining each of the facial feature(s), the body feature(s), the spatial feature(s), and the speech feature(s) for each individual in the group of individuals. In this regard, the step 106 of determining a group characteristic information comprises determining the group characteristic information based on each of the facial feature(s), the body feature(s), the spatial feature(s), and the speech feature(s) associated with each individual in the group of individuals determined.

Figure 2:
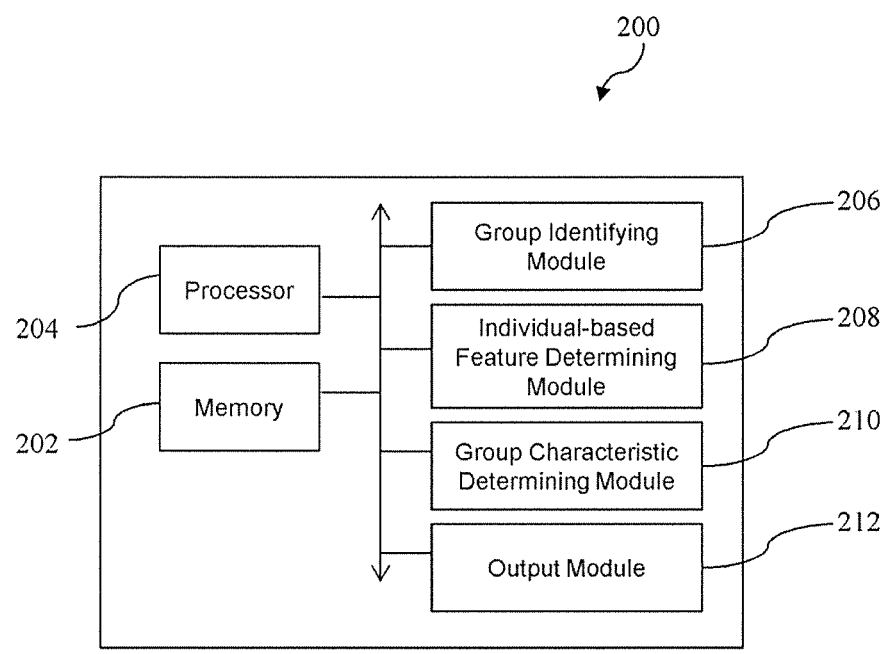
FIG. 2 depicts a schematic block diagram of a system for generating an output with respect to a group of individuals according to various embodiments of the present invention.

FIG. 2 depicts a schematic block diagram of a system 200 for generating an output with respect to a group of individuals according to various embodiments of the present invention, such as corresponding to the method 100 for generating an output with respect to a group of individuals as described hereinbefore according to various embodiments of the present invention.

The system 200 comprises a memory 202, and at least one processor 204 communicatively coupled to the memory 202 and configured to: identify the group of individuals amongst a plurality of individuals in an area being monitored by one or more sensors; determine, for each individual in the group of individuals, one or more individual-based features associated with the individual based on sensing data obtained from the one or more sensors; determine a group characteristic information associated with the group of individuals based on the one or more individual-based features determined for each individual in the group; and generate the output based on the group characteristic information determined for the group of individuals.

It will be appreciated by a person skilled in the art that the at least one processor 204 may be configured to perform the required functions or operations through set(s) of instructions (e.g., software modules) executable by the at least one processor 204 to perform the required functions or operations. Accordingly, as shown in FIG. 2, the system 200 may further comprise a group identifying module or circuit 206 configured to identify the group of individuals amongst a plurality of individuals in an area being monitored by one or more sensors; an individual-based feature determining module or circuit 208 configured to determine, for each individual in the group of individuals, one or more individual-based features associated with the individual based on sensing data obtained from the one or more sensors; a group characteristic determining module or circuit 210 configured to determine a group characteristic information associated with the group of individuals based on the one or more individual-based features determined for each individual in the group; and an output module 212 configured to generate the output based on the group characteristic information determined for the group of individuals. For example, the output module 212 may generate an output in the form of a content, an alert or an effect based on the group characteristic information, or in the form of a signal or message comprising the group characteristic information for transmission to one or more devices or systems configured for specific application(s), such that the one or more devices or systems generate their output based on the signal or message received.

In various embodiments, the system 200 corresponds to the method 100 as described hereinbefore with reference to FIG. 1, therefore, various functions or operations configured to be performed by the least one processor 204 may correspond to various steps of the method 100 described in hereinbefore, and thus need not be repeated with respect to the system 200 for clarity and conciseness. In other words, various embodiments described herein in context of the methods are analogously valid for the respective systems or devices, and vice versa.

For example, in various embodiments, the memory 202 may further have stored therein a group identifying module 206, an individual-based feature determining module 208, a group characteristic determining module 210, and/or an output module 212, as described herebefore with respect to the method 100 according to various embodiments of the present invention, which are executable by the at least one processor 204 to perform the corresponding functions/operations as described.

A computing system, a controller, a microcontroller or any other system providing a processing capability may be provided according to various embodiments in the present disclosure. Such a system may be taken to include one or more processors and one or more computer-readable storage mediums. For example, the system 200 described hereinbefore may be a device or a system including a processor (or controller) 204 and a computer-readable storage medium (or memory) 202 which are for example used in various processing carried out therein as described herein. A memory or computer-readable storage medium used in various embodiments may be a volatile memory, for example a DRAM (Dynamic Random Access Memory) or a non-volatile memory, for example a PROM (Programmable Read Only Memory), an EPROM (Erasable PROM), EEPROM (Electrically Erasable PROM), or a flash memory, e.g., a floating gate memory, a charge trapping memory, an MRAM (Magnetoresistive Random Access Memory) or a PCRAM (Phase Change Random Access Memory).

In various embodiments, a "circuit" may be understood as any kind of a logic implementing entity, which may be special purpose circuitry or a processor executing software stored in a memory, firmware, or any combination thereof. Thus, in an embodiment, a "circuit" may be a hard-wired logic circuit or a programmable logic circuit such as a programmable processor, e.g., a microprocessor (e.g., a Complex Instruction Set Computer (CISC) processor or a Reduced Instruction Set Computer (RISC) processor). A "circuit" may also be a processor executing software, e.g., any kind of computer program, e.g., a computer program using a virtual machine code, e.g., Java. Any other kind of implementation of the respective functions which will be described in more detail below may also be understood as a "circuit" in accordance with various alternative embodiments. Similarly, a "module" may be a portion of a system according to various embodiments in the present invention and may encompass a "circuit" as above, or may be understood to be any kind of a logic-implementing entity therefrom.

Some portions of the present disclosure are explicitly or implicitly presented in terms of algorithms and functional or symbolic representations of operations on data within a computer memory. These algorithmic descriptions and functional or symbolic representations are the means used by those skilled in the data processing arts to convey most effectively the substance of their work to others skilled in the art. An algorithm is here, and generally, conceived to be a self-consistent sequence of steps leading to a desired result. The steps are those requiring physical manipulations of physical quantities, such as electrical, magnetic or optical signals capable of being stored, transferred, combined, compared, and otherwise manipulated.

Unless specifically stated otherwise, and as apparent from the following, it will be appreciated that throughout the present specification, discussions utilizing terms such as "identifying", "determining", "generating", "computing", "presenting", "providing", or the like, refer to the actions and processes of a computer system, or similar electronic device, that manipulates and transforms data represented as physical quantities within the computer system into other data similarly represented as physical quantities within the computer system or other information storage, transmission or display devices.

The present specification also discloses a system, a device or an apparatus for performing the operations/functions of the methods described herein. Such a system, device or apparatus may be specially constructed for the required purposes, or may comprise a general purpose computer or other device selectively activated or reconfigured by a computer program stored in the computer. The algorithms presented herein are not inherently related to any particular computer or other apparatus. Various general-purpose machines may be used with computer programs in accordance with the teachings herein. Alternatively, the construction of more specialized apparatus to perform the required method steps may be appropriate.

In addition, the present specification also at least implicitly discloses a computer program or software/functional module, in that it would be apparent to the person skilled in the art that the individual steps of the methods described herein may be put into effect by computer code. The computer program is not intended to be limited to any particular programming language and implementation thereof. It will be appreciated that a variety of programming languages and coding thereof may be used to implement the teachings of the disclosure contained herein. Moreover, the computer program is not intended to be limited to any particular control flow. There are many other variants of the computer program, which can use different control flows without departing from the spirit or scope of the invention.

It will be appreciated by a person skilled in the art that various modules described herein (e.g., a group identifying module 206, an individual-based feature determining module 208, a group characteristic determining module 210, and/or an output module 212) may be software module(s) realized by computer program(s) or set(s) of instructions executable by a computer processor to perform the required functions, or may be hardware module(s) being functional hardware unit(s) designed to perform the required functions. It will also be appreciated that a combination of hardware and software modules may be implemented.

Furthermore, one or more of the steps of a computer program/module or method described herein may be performed in parallel rather than sequentially. Such a computer program may be stored on any computer readable medium. The computer readable medium may include storage devices such as magnetic or optical disks, memory chips, or other storage devices suitable for interfacing with a general purpose computer. The computer program when loaded and executed on such a general-purpose computer effectively results in an apparatus that implements the steps of the methods described herein.

In various embodiments, there is provided a computer program product, embodied in one or more computer-readable storage mediums (non-transitory computer-readable storage medium), comprising instructions (e.g., a group identifying module 206, an individual-based feature determining module 208, a group characteristic determining module 210, and/or an output module 212) executable by one or more computer processors to perform a method 100 for generating an output with respect to a group of individuals as described hereinbefore with reference to FIG. 1. Accordingly, various computer programs or modules described herein may be stored in a computer program product receivable by a system (e.g., a computer system or an electronic device) therein, such as the system 200 as shown in FIG. 2, for execution by at least one processor 204 of the system 200 to perform the required or desired functions.

The software or functional modules described herein may also be implemented as hardware modules. More particularly, in the hardware sense, a module is a functional hardware unit designed for use with other components or modules. For example, a module may be implemented using discrete electronic components, or it can form a portion of an entire electronic circuit such as an Application Specific Integrated Circuit (ASIC). Numerous other possibilities exist. Those skilled in the art will appreciate that the software or functional module(s) described herein can also be implemented as a combination of hardware and software modules.

Figure 3:
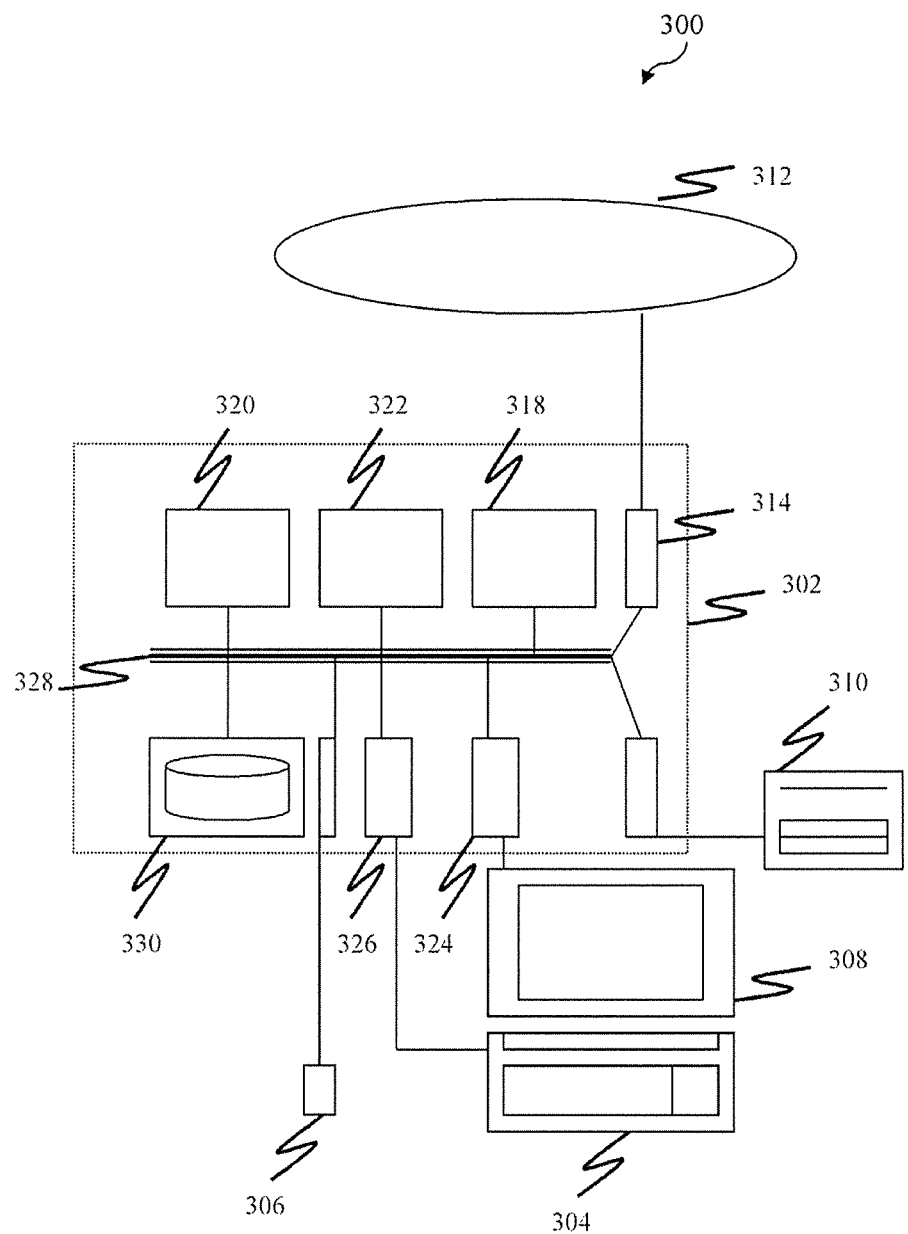
FIG. 3 depicts a schematic drawing of an example computer system in which the system as shown in FIG. 2 may be implemented.

In various embodiments, the system 200 may be realized by any computer system (e.g., portable or desktop computer system), such as a computer system 300 as schematically shown in FIG. 3 as an example only and without limitation. Various methods/steps or functional modules (e.g., a group identifying module 206, an individual-based feature determining module 208, a group characteristic determining module 210, and/or an output module 212) may be implemented as software, such as a computer program being executed within the computer system 300, and instructing the computer system 300 (in particular, one or more processors therein) to conduct the methods/functions of various embodiments described herein. The computer system 300 may comprise a computer module 302, input modules, such as a keyboard 304 and a mouse 306, and a plurality of output devices such as a display 308, and a printer 310. The computer module 302 may be connected to a computer network 312 via a suitable transceiver device 314, to enable access to e.g. the Internet or other network systems such as Local Area Network (LAN) or Wide Area Network (WAN). The computer module 302 in the example may include a processor 318 for executing various instructions, a Random Access Memory (RAM) 320 and a Read Only Memory (ROM) 322. The computer module 302 may also include a number of Input/Output (I/O) interfaces, for example I/O interface 324 to the display 308, and I/O interface 326 to the keyboard 304. The components of the computer module 302 typically communicate via an interconnected bus 328 and in a manner known to the person skilled in the relevant art.

It will be appreciated by a person skilled in the art that the terminology used herein is for the purpose of describing various embodiments only and is not intended to be limiting of the present invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

In order that the present invention may be readily understood and put into practical effect, various example embodiments of the present invention will be described hereinafter by way of examples only and not limitations. It will be appreciated by a person skilled in the art that the present invention may, however, be embodied in various different forms or configurations and should not be construed as limited to the example embodiments set forth hereinafter. Rather, these example embodiments are provided so that this disclosure will be thorough and complete, and will fully convey the scope of the present invention to those skilled in the art.

In particular, for better understanding of the present invention and without limitation or loss of generality, various example embodiments of the present invention will now be described with respect to the output being a targeted advertisement content. However, as mentioned hereinbefore, it will be appreciated by a person skilled in the art that the present invention is not limited to the output being a targeted advertisement content, and the output generated may be for various other applications as desired or as appropriate, as long as the output is desired to be dependent or based on the group characteristic information associated with a group of individuals determined, such as but not limited to, a targeted security alert and an environment setting.

Figure 4:
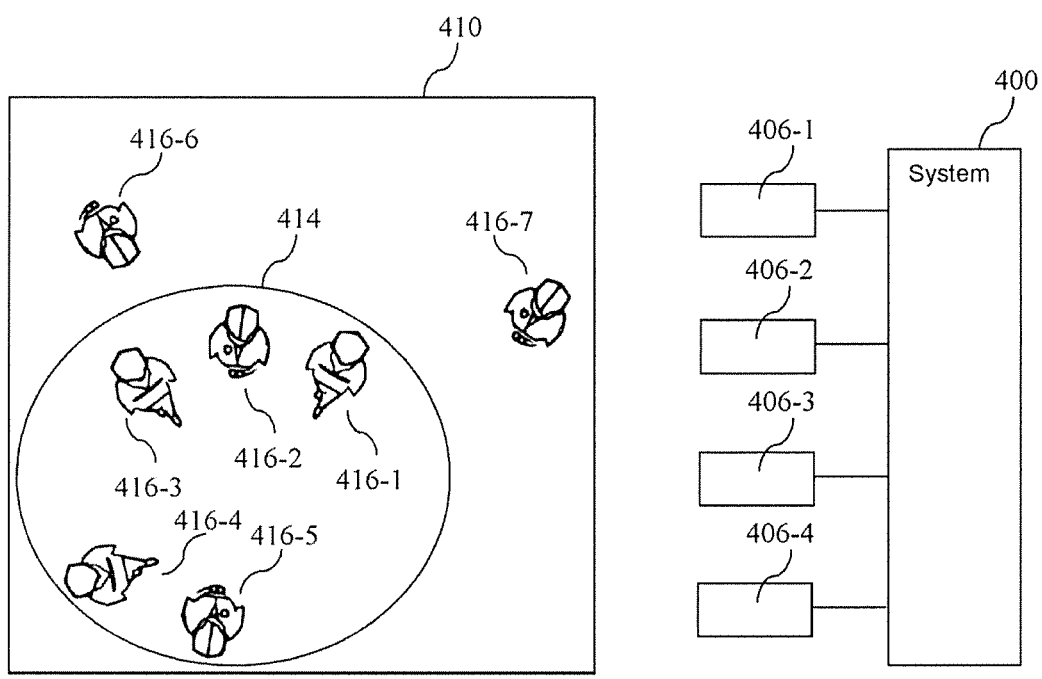
FIG. 4 depicts a schematic drawing illustrating an example overview of a method for generating an output with respect to a group of individuals according to various example embodiments of the present invention.

FIG. 4 depicts a schematic drawing illustrating an example overview of a method for generating an output with respect to a group of individuals according to various example embodiments of the present invention. As shown in the example of FIG. 4, there may be provided a system 400 (e.g., corresponding to the system 200 as described hereinbefore according to various embodiments) for generating an output with respect to a group of individuals. In the example, the system 400 may comprise, or may be communicatively coupled to, one or more sensors. The sensor may be any type of sensors as desired or as appropriate for obtaining or collecting the desired data or information, such as but not limited to, a motion sensing device 406-1 (e.g., MICROSOFT KINECT or the like) for collecting/generating motion data of individual(s), an image capturing device 406-2 (e.g., a camera) for capturing image data of individual(s), an audio capturing device 406-3 (e.g., a microphone) for capturing audio data from individual(s), and/or a range sensing device 406-4 (e.g., LIDAR sensor or the like) for generating distance data (i.e., point cloud data) of individual(s). In various example embodiments, a positioning system (e.g., WiFi positioning) may be provided for determining the position/location of individual(s). It will be appreciated by a person skilled in the art that the different sensors are not necessarily separate units and may be realized as one integrated unit as appropriate, such as an integrated unit with two or more of motion sensing, image capturing, distance (range) capturing and audio capturing capabilities. Furthermore, it will be appreciated by a person skilled in the art that individual-based features may be derived based on data (e.g., sensing data) obtained from one sensor or a combination of different types of sensors (different types of modalities) as desired or as appropriate. By way of example only, individual-based features may be determined based on data obtained from a camera, a combination of a camera and a ToF sensor, a combination of a camera and a positioning system, and so on. For example, ToF sensor may provide better localization, positioning and body orientation than a RGB camera, but the type of sensors used may depend on various factors, such as the degree of accuracy required and cost constraints.

The one or more sensors may be arranged to monitor individuals in a designated area 410. The system 400 may be configured to (e.g., by a group identifying module 206 therein) identify a group of individuals amongst a plurality of individuals 416-1 to 416-7 in the area 410 being monitored by the one or more sensors, such as based on sensing data obtained from the one or more sensors. In the example, the system 400 identifies a group 414 of individuals 416-1 to 416-5 as shown encircled in FIG. 4. It can also be observed that individuals 416-6 and 416-7 are not identified as part of the group 414. In various example embodiments, individual 416-6 may be assigned to a second group by itself and individual 416-7 may be assigned to a third group by itself. For example, in the case of the system 400 being an advertisement system, the system 400 may generate a targeted advertisement content based on the group characteristic information determined for the group 414 of individuals, which may then be displayed on a display screen.

In various example embodiments, the targeted advertisement content (or an executable link to the targeted advertisement) may be sent to client devices (not shown) associated with the group 414 of individuals via any appropriate wireless protocol known in the art, such as but not limited to, a wireless push notification via Wi-Fi or Bluetooth. As a result, the group 414 of individuals may then be able to view the targeted advertisement content on their respective client device.

Figure 5:
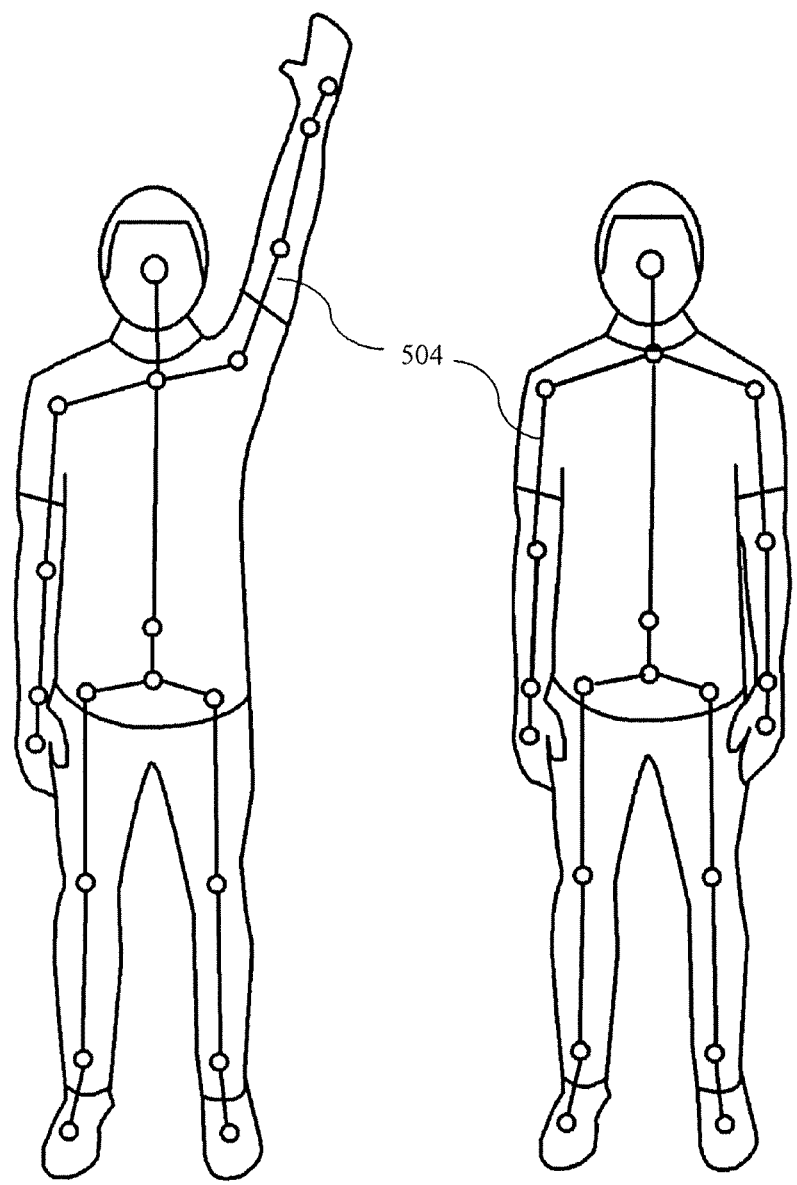
FIG. 5 depicts a schematic drawing of an example skeleton model or representation generated for an individual at two example postures according to various example embodiments of the present invention.

FIG. 5 depicts a schematic drawing of an example skeleton model or representation 504 generated for an individual at two example postures. It will be appreciated by a person skilled in the art that a skeleton model (e.g., as shown in FIG. 5 or any other suitable or appropriate types of skeleton model) for an individual may be determined or generated based on various conventional techniques known in the art, that is, suitable or appropriate conventional techniques thereof would be understood by a person skilled in the art and thus need not be described in detail herein. As shown, the skeleton model 504 has a multiple branching structure comprises a plurality of nodes at various points corresponding to various joints/parts of a skeleton, each node being an intermediate node or an end node, and a branch (arc) connecting appropriate/selected pairs of adjacent nodes.

For illustration purpose and without limitation, an example technique of identifying a group of individuals amongst a plurality of individuals will now be described according to various example embodiments of the present invention based on the skeleton model. The example technique may include a first step of determining (e.g., estimating) a separation (e.g., pairwise distance) between each adjacent pair of individuals (based on the respective skeleton models generated) in the area (or scene) being monitored; a second step of determining (e.g., computing) an orientation of each individual (i.e., the orientation of the corresponding skeleton model generated) in the area being monitored; and a third step of grouping individuals into one or more groups based on a predetermined separation condition and a predetermined orientation condition.

In relation to the above-mentioned first step, for example, the three-dimensional (3D) position of each skeleton model (e.g., Cartesian coordinates of each node of the skeleton model) may be determined based on a range sensor (e.g., a ToF sensor). It will be appreciated by a person skilled in the art that any suitable node of the skeleton model may be chosen to represent the position of the skeleton model. By way of an example, the node (node coordinate) corresponding to the thorax position of the skeleton model may be selected to represent the position of the skeleton model, which may also be referred to as the representative node. Based on the representative node selected, the pairwise distance between a first individual (first skeleton model) and a second individual (second skeleton model) may then be determined, for example, based on the following equation:

$$D = \sqrt{(X_1-X_2)^2+(Y_1-Y_2)^2+(Z_1-Z_2)^2} \quad \text{(Equation 1)}$$

where D is the pairwise distance, $(X_1, Y_1, Z_1)$ is the Cartesian coordinate of the first individual (first skeleton model), and $(X_2, Y_2, Z_2)$ is the Cartesian coordinate of the second individual (second skeleton model).

Figure 6:
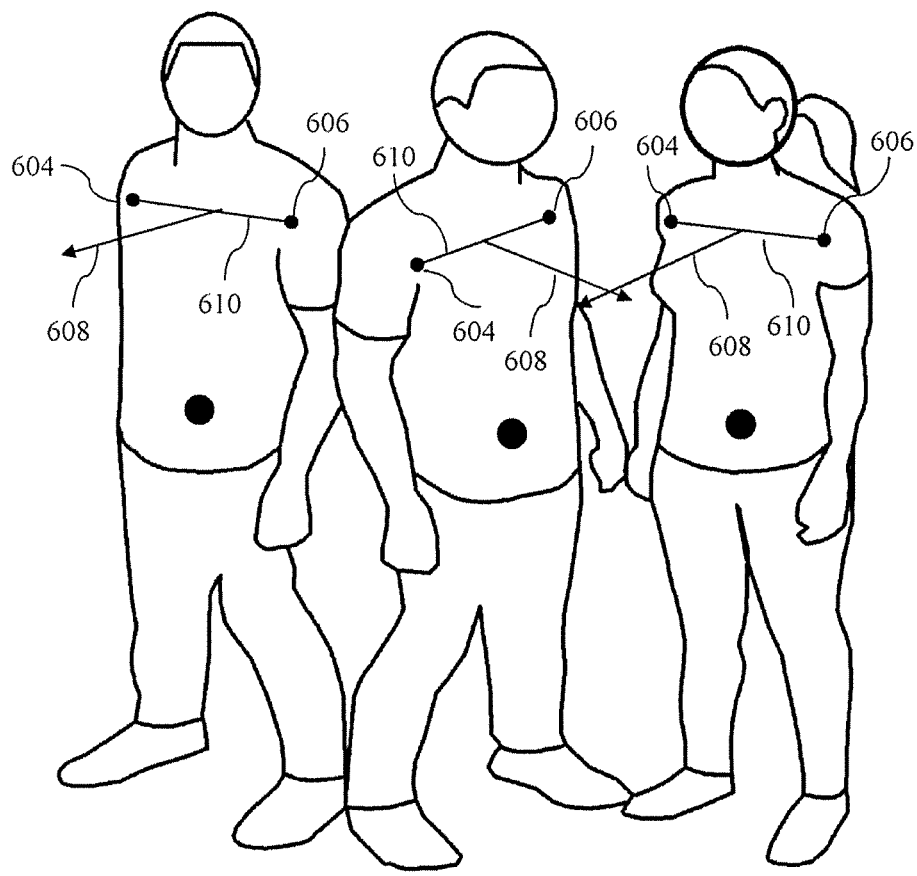
FIG. 6 depicts a schematic drawing of three individuals along with their respective orientation shown according to various example embodiments of the present invention.

FIG. 6 depicts a schematic drawing of three individuals along with their respective orientation shown according to various example embodiments of the present invention. For example, in relation to the above-mentioned second step, determining the orientation (representative orientation) of an individual may include locating a left shoulder node 604 corresponding the left shoulder end of the skeleton model and a right shoulder node 606 corresponding to the right shoulder end of the skeleton model, and generating a direction vector 608 perpendicular to a line 610 (e.g., from a center/middle point thereof) joining/connecting the left shoulder node 604 and right shoulder node 606 of the skeleton model. The direction vector 608 determined may thus represent the orientation of the individual. In various example embodiments, the direction vector 608 corresponds to the direction in which the individual is facing (facing direction). It will be appreciated by a person skilled in the art that the direction vector 608 may be determined or generated based on various conventional techniques known in the art, that is, suitable or appropriate conventional techniques thereof would be understood by a person skilled in the art and thus need not be described in detail herein. For example, a conventional skeleton tracker may provide a facing direction. As another example, a facing direction may be determined based on a face detector of an image capturing device.

Figure 7:
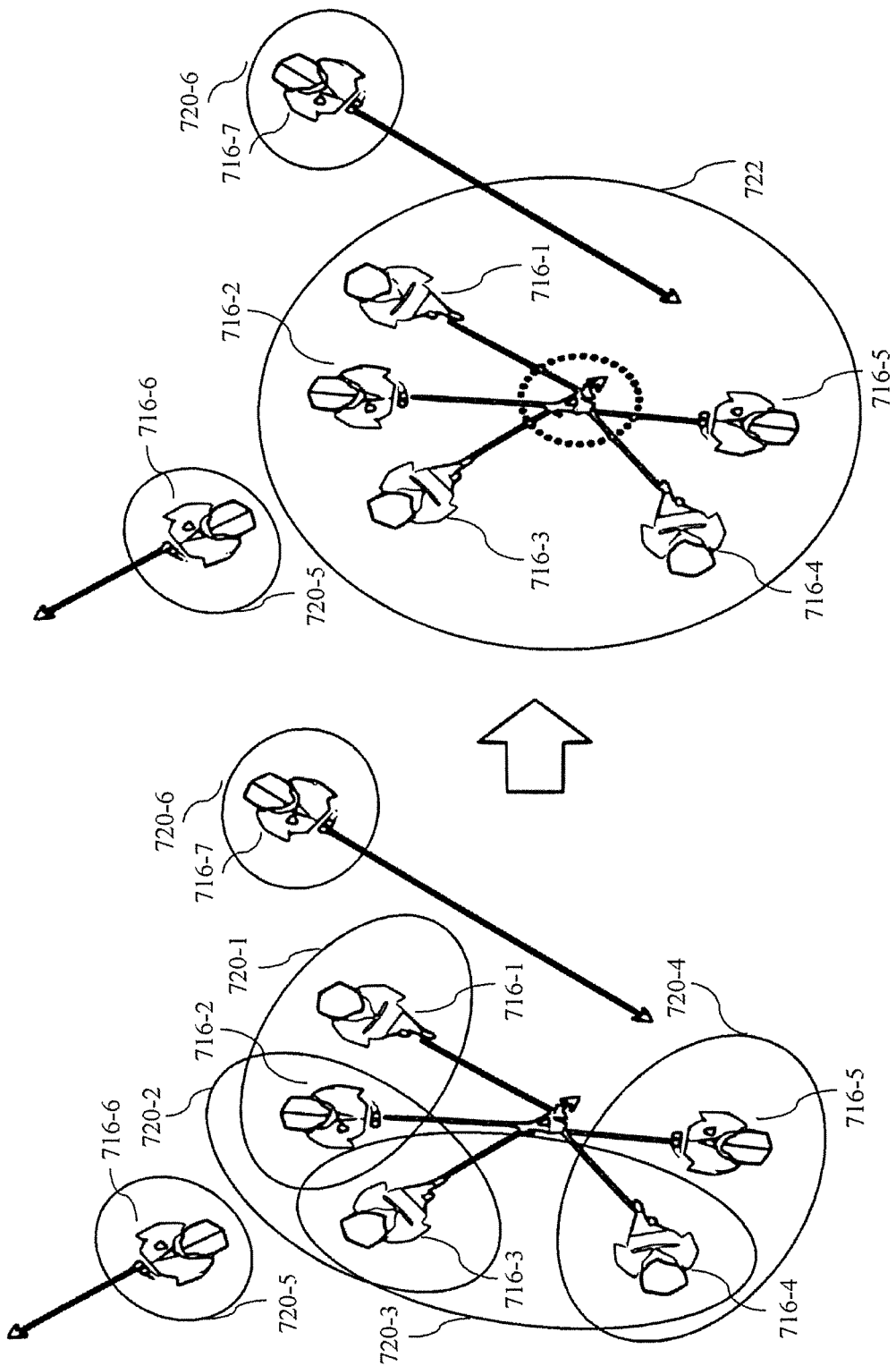
FIG. 7 depicts a schematic drawing of a top view of a plurality of individuals located in an area being monitored, along with their respective orientation shown, according to various example embodiments of the present invention.

FIG. 7 depicts a schematic drawing of a top view of a plurality of individuals located in an area being monitored, along with their respective orientation shown, according to various example embodiments of the present invention. In relation to the above-mentioned third step, grouping individuals into one or more groups may include grouping each adjacent pair of individuals as one group if the pair of individuals satisfy both the predetermined separation condition and the predetermined orientation condition. For example, as shown in FIG. 7, individuals 716-1 to 716-7 may initially be grouped into six groups 720-1 to 720-6. For groups 720-1 to 720-4, each corresponding adjacent pair of individuals satisfy both the predetermined separation condition (e.g., their separation is within a predetermined separation) and the predetermined orientation condition (e.g., their orientations are considered to be toward each other, e.g., converges towards a point), and thus the respective pair of individuals form a respective group. On the other hand, for example, individuals 716-7 and 716-1 do not satisfy the predetermined separation condition and individuals 716-6 and 716-2 or 716-3 do not satisfy the predetermined orientation condition, and thus the respective pair of individuals do not form a respective group. In addition, initial groups 720-1 and 720-2 share a common individual, initial groups 720-2 and 720-3 share a common individual, and initial groups 720-3 and 720-4 share a common individual (that is, initial groups 720-1 to 720-4 are linked by at least one common individual), and thus, groups 720-1 and 720-4 may merge to form one group 722 of individuals 716-1 to 716-5. On the other hand, groups 720-5 and 720-6 are each not merged with any other group(s) as they do not share any common individual with any other group. Accordingly, in the example, the plurality of individuals 716-1 to 716-7 are grouped into three separate groups 722, 720-5, and 720-6. As shown in FIG. 7, an isolated individual 716-6 or 716-7 may also be considered as a group.

Figure 8:
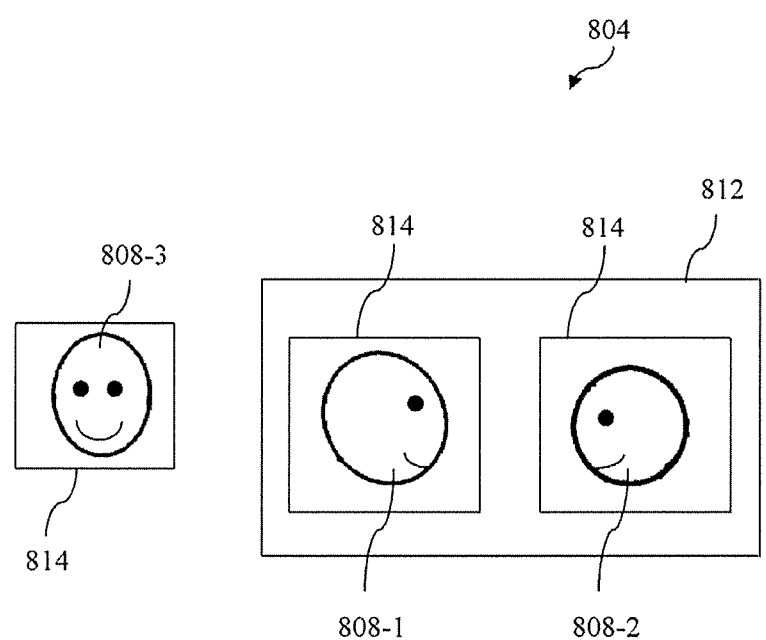
FIG. 8 depicts a schematic drawing of face models or representations generated for three individuals according to various example embodiments of the present invention.

As mentioned hereinbefore, it will be appreciated to a person skilled in the art that the present invention is not limited to a skeleton model for representing an individual and various other types of schematic models may be used as desired or as appropriate, as long as the position and orientation of the individual can be derived from the schematic model. As another example, FIG. 8 depicts a schematic drawing of face models or representations 804, including eye portions (e.g., eye nodes), generated for three individuals in a group. It will be appreciated by a person skilled in the art that a face model as appropriate or as desired (e.g., two-dimensional or three-dimensional) for an individual may be determined or generated based on various conventional techniques known in the art, that is, suitable or appropriate conventional techniques thereof would be understood by a person skilled in the art and thus need not be described in detail herein.

Similarly, a group of individuals may be identified based on the face model according to various example embodiments of the present invention. The example technique may include a first step of determining (e.g., estimating) a separation (e.g., pairwise distance) between each adjacent pair of individuals (based on the face models generated) in the area (or scene) being monitored; a second step of determining (e.g., computing) an orientation of each individual (i.e., the orientation of the corresponding face mode generated) in the area being monitored; and a third step of grouping individuals into one or more groups based on a predetermined separation condition and a predetermined orientation condition. Similarly, grouping individuals into one or more groups may include grouping each adjacent pair of individuals as one group if the pair of individuals satisfy both the predetermined separation condition and the predetermined orientation condition.

For example, as shown in FIG. 8, individuals 808-1 and 808-2 is grouped into one group as they were found to satisfy both the predetermined separation condition (e.g., their separation is within a predetermined separation) and the predetermined orientation condition (e.g., their orientations are considered to be toward each other, e.g., converges towards a point). On the other hand, for example, individual 808-3 was not found to satisfy the predetermined separation condition with respect to individual 808-2 and was not found to satisfy the predetermined orientation condition with respect to individual 808-1, and thus individual 808-3 does not form a group with either individual 808-1 or 808-2. In various example embodiments, to enhance visual effects, a group box or frame 812 may be generated for enclosing or surrounding both individuals 808-1 and 808-2 to indicate that they belong to a group. Furthermore, in various example embodiments, a face box or frame 814 may also be generated for enclosing or surrounding the respective face model whereby the size of the box may indicate a distance to a reference point (e.g. the image capturing device). For example, a smaller face box enclosing a face model may indicate that the corresponding individual is further away from a reference point than a larger face box. In the example of FIG. 8, both individuals 808-1 and 808-2 may be at substantially the same distance away from a reference point and individual 808-3 may be further from the reference point than individuals 808-1 and 808-2.

Figure 9:
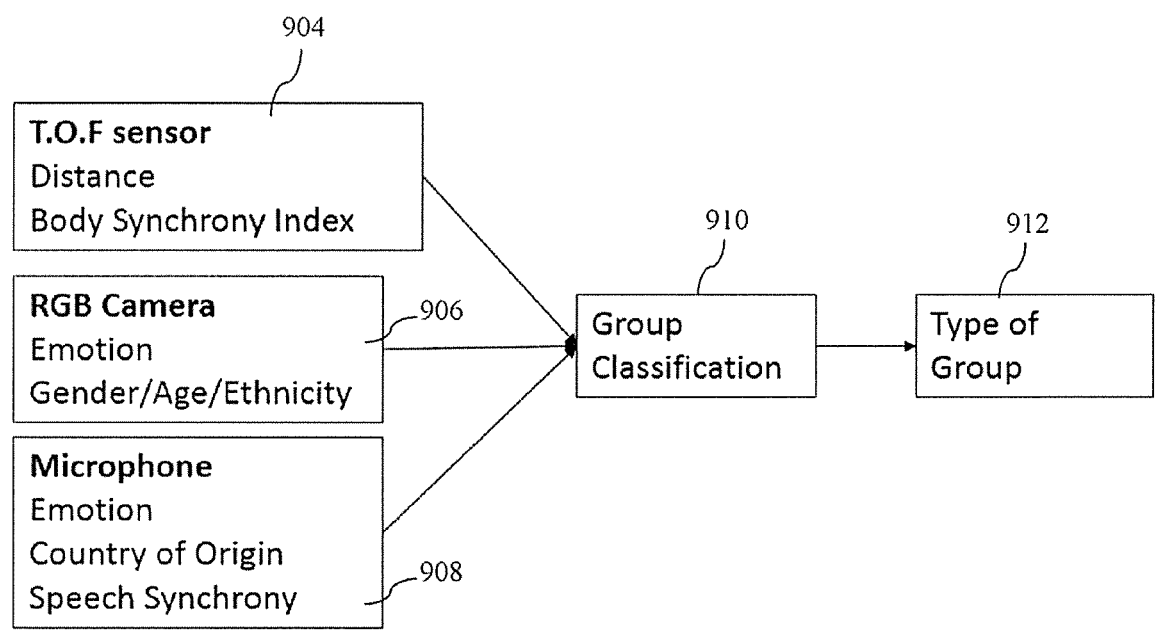
FIG. 9 depicts a block diagram illustrate an example technique of determining a group classification information associated with a group of individuals according to various example embodiments of the present invention.

FIG. 9 depicts a block diagram illustrate an example technique of determining a group classification information associated with a group of individuals based on a plurality of types of features determined for the group according to various example embodiments of the present invention. As shown, a plurality of types of features (including individual-based and/or group based features) may be determined, including one or more body features 904, one or more facial features 906, and one or more speech features 908. By way of examples only and without limitations, the one or more body features 904 may be determined based on a range sensor (e.g., ToF sensor) and may include, for example, a distance of an individual to the range sensor and/or a body movement synchrony index associated with the group of individuals. In various example embodiments, a motion sensor may be provided to obtain motion data of the individuals in the group, for example, for determining the body movement synchrony index associated the group. The one or more facial features 906 may be determined based on an image capturing device (e.g., a camera) and may include, for example, an emotional state of the individual, the gender of the individual, the age of the individual and/or the ethnicity of the individual. By way of an example and without limitation, an emotion estimating method based on facial expression is described in U.S. patent application Ser. No. 15/288,866 titled "Emotion Estimating Method, Emotion Estimating Apparatus, and Recording Medium Storing Program" filed by Panasonic Intellectual Property Corporation of Ame on 7 Oct. 2016, the contents of which are hereby incorporated by reference in their entirety for all purposes. The one or more speech features 908 may be determined based on an audio capturing device and may include, for example, an emotional state of the individual, the ethnicity of the individual, the speech synchrony index associated with the group. It will be appreciated by a person skilled in the art that the present invention is not limited to the above-mentioned individual-based or group-based features of an individual and other types of individual-based or group-based features may be determined as desired or as appropriate. For example, possible types of body features 904 may further include the proxemics (e.g., distance to the group center×weight of the individual), the body openness index, the quantity of motion, and so on. Possible types of facial features 906 may further include a gaze pattern (e.g., the number of time an individual is being looked at by other individuals in the group). Possible types of speech features 908 may further include loudness, speech duration, how formal or informal is the speech, personality analysis, and so on. As can be appreciated, there is generally no limit to the possible types of individual-based or group-based features that may be evaluated.

For example, with respect to the speech features 908, it will be appreciated by a person skilled in the art that the location of one or more sources (and/or direction) of an audio/sound from one or more individuals detected may be determined based on various conventional audio source localization techniques known in the art, that is, suitable or appropriate conventional techniques thereof would be understood by a person skilled in the art and thus need not be described in detail herein. As a result, for example, audio/sound from a particular individual detected may be assigned to the particular individual by comparing or matching the location (and/or direction) of the source of the audio/sound determined with the location (and/or direction) of the particular individual determined. As a non-limiting example, for a sound from an individual, a linear function may be computed based on the direction of the sound determined, and for each individual in the area being monitored, a corresponding linear function may also be computed that passes through the individual (e.g., based on the position of the corresponding skeleton model). Accordingly, the sound may then be assigned to the individual having an associated linear function which is closest (e.g., best matches) the linear function of the sound.

It can also be appreciated by a person skilled in the art that each type of individual-based or group based features desired may be determined based on any appropriate technique known in the art and thus need not be described herein.

As shown in FIG. 9, after the plurality of types of features have been determined, a classifier 910 may then classify the group based on a combination of the plurality of types of features received and generate a classification result/output 912 as the group characteristic information (e.g., type of group) associated with the group.

By way of an example only and without limitation, a specific example technique of classifying a group of individuals will now be described. The example technique includes a first step of determining (e.g., estimating) the separation between each adjacent pair of individuals in the group; a second step of determining a center position of the group; a third step of computing the emotional state of each individual in the group; a fourth step of determining the attire of each individual in the group; a fifth step of determining the gender, age, and ethnicity of each individual in the group; a sixth step of determining a body synchrony index associated with the group, for example, by computing the average skeleton position (e.g., average joint angle) and computing the deviation for each individual; a seventh step of determining a speech synchrony index associated with the group, for example, based on the intonation, the number of time individuals speak at the same time, whether individuals are taking turn to speak, and so on; and an eighth step of classifying the group based on a combination of the types of features determined to generate a classification result/output as the group characteristic information associated with the group.

For illustration purpose only and without limitation, an example leader detection technique for detecting a leader in the group will now be described according to an example embodiment of the present invention. For example, the example leader detection technique may be configured taking into account one or more (e.g., a weighted combination) of the following factors: a leader may be the oldest in the group; a leader may be gazed at by other individuals in the group more often; a leader may be located close to a center of the group; a leader may be speaking more often; a leader may have an extraverted personality; and so on. For example, various movements such as head nods may also be useful cues in detecting a leader in a group. In the example, for each individual in the group, a leader score may be determined based on the following example equation:

$$w_0*\text{gender}_{score}+w_1*\text{age}_{score}+w_2*\text{proxemics}_{score}+\\ w_3*\text{Loudness}_{score}+w_4*\text{Extraversion}_{score}+\\ w_5*\text{Speech}_{score} \quad\quad\quad\quad\text{(Equation 2)}$$

where $w_0$ to $w_5$ are the respective weights assigned to each type of features for determining the leader in the group.

The leader may then be determined to be the individual in the group that obtained the highest score based on Equation 2. It will be appreciated by a person skilled in the art that the respective weights can be set as desired or as appropriate based on various factors or circumstances (e.g., the location of the group, the country, the number of people in the group, and so on). In various example embodiments, the weights can be determined or learned using a linear regression model. In various example embodiments, the technique of detecting a leader may also be implemented as a classification technique based on various machine learning methods or algorithms known in the art.

Figure 10A:
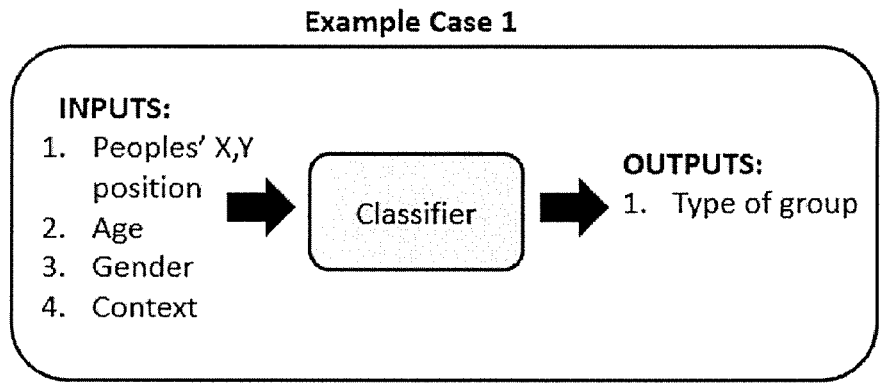
FIGS. 10A to 10C depict three schematic block diagrams of three example cases, respectively, illustrating example types of features of individuals in a group and the example group characteristic information that may be determined for the group based on a classification of such example types of features, according to various example embodiments of the present invention.
Figure 10B:
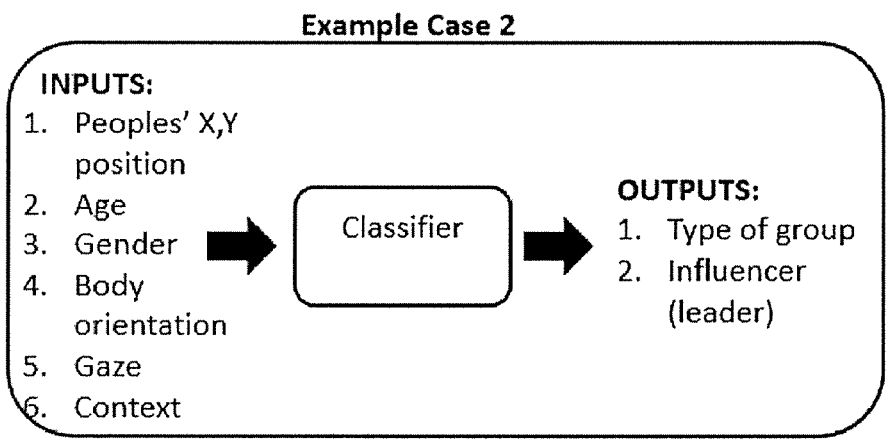
Figure 10C:
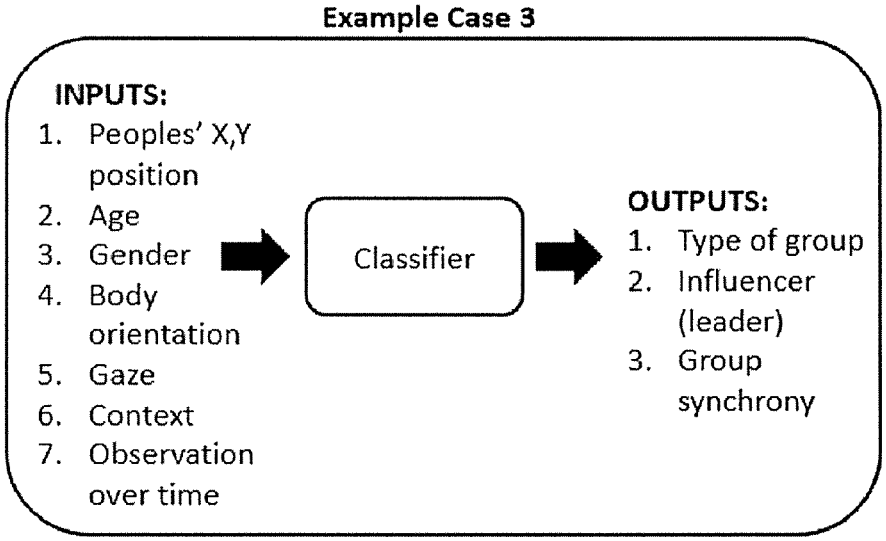

By way of examples only and without limitations, FIGS. 10A to 10C depict three schematic block diagrams of three example cases, respectively, illustrating example types of features of individuals in a group and the example group characteristic information that may be determined for the group based on a classification of such example types of features. For example, the inputs to a classifier may include one or more of the position (coordinates), age, gender, context, body orientation gaze pattern, and an observation over time of individuals in the group. For example, the outputs to the classifier may include one or more of the type (e.g., relationship) of group, an influencer (e.g., leader) of the group, and the group synchrony. For example, an individual analysis may be determine one or more features such as age, gender, ethnicity, clothing, and emotion of the individual. For example, a group analysis may determine one or more features such as proxemics (e.g., who is close to who), posture (e.g., who has closed/open posture), action recognition, head pose (who is looking at who), and voice patterns. For example, various group classification information may then be determined, such as the relationship of the group (e.g., couple, colleagues, father-child, friends, and so on), the influencer (e.g., leader) in the group, the activity of the group (e.g., shopping, eating, travelling, and so on), and the type of content that may be advertised to the group based on the context determined (e.g., restaurants, shopping, and so on).

Figure 11:
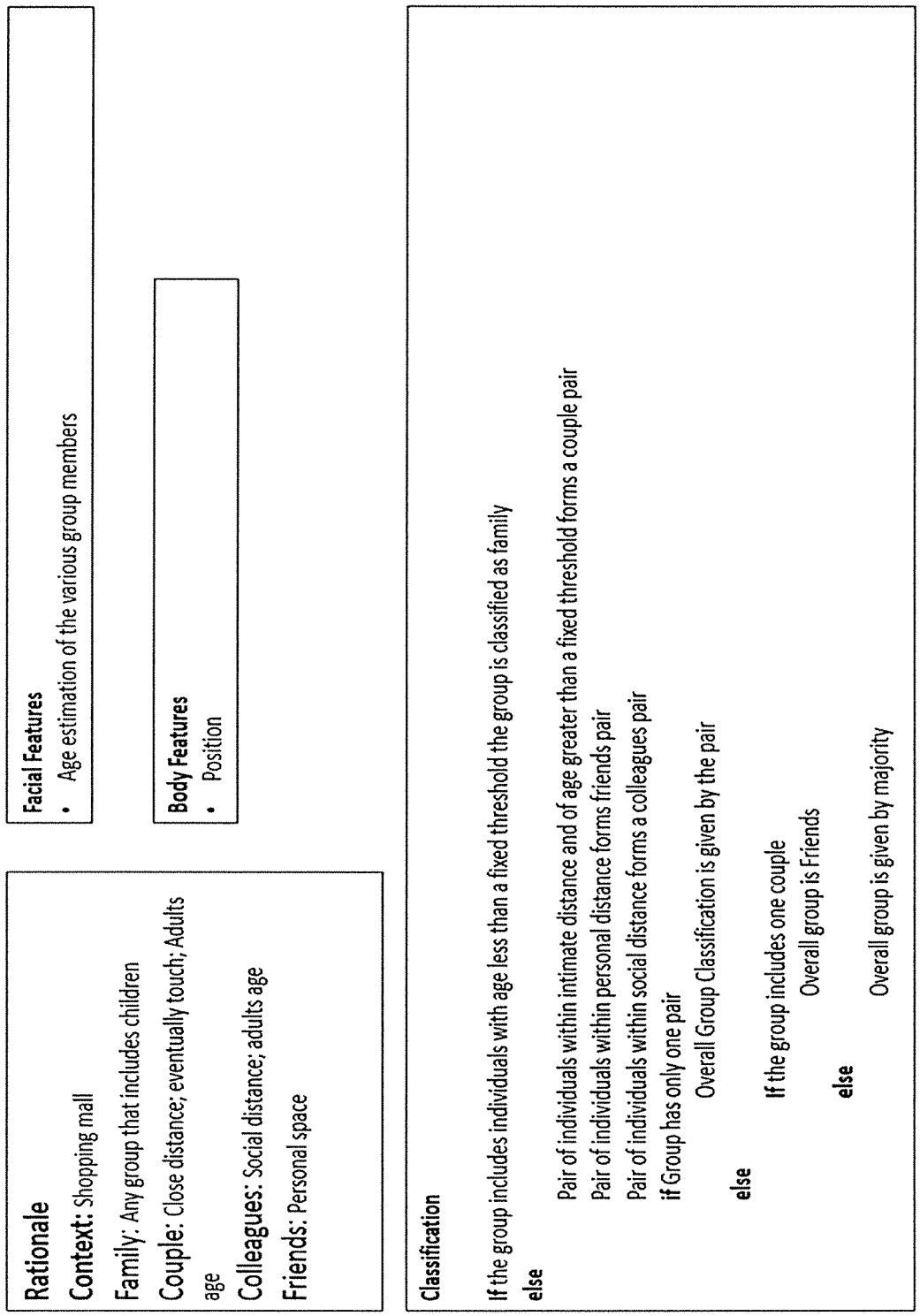
FIG. 11 depicts an example group classification technique configured to output a group classification information based on various example types of features of the individuals in the group, according to various example embodiments of the present invention.

By way of an example only and without limitation, FIG. 11 depicts an example group classification technique configured to output a group classification information (e.g., friend, family, or colleague) based on various example types of features of the individuals in the group.

Figure 12:
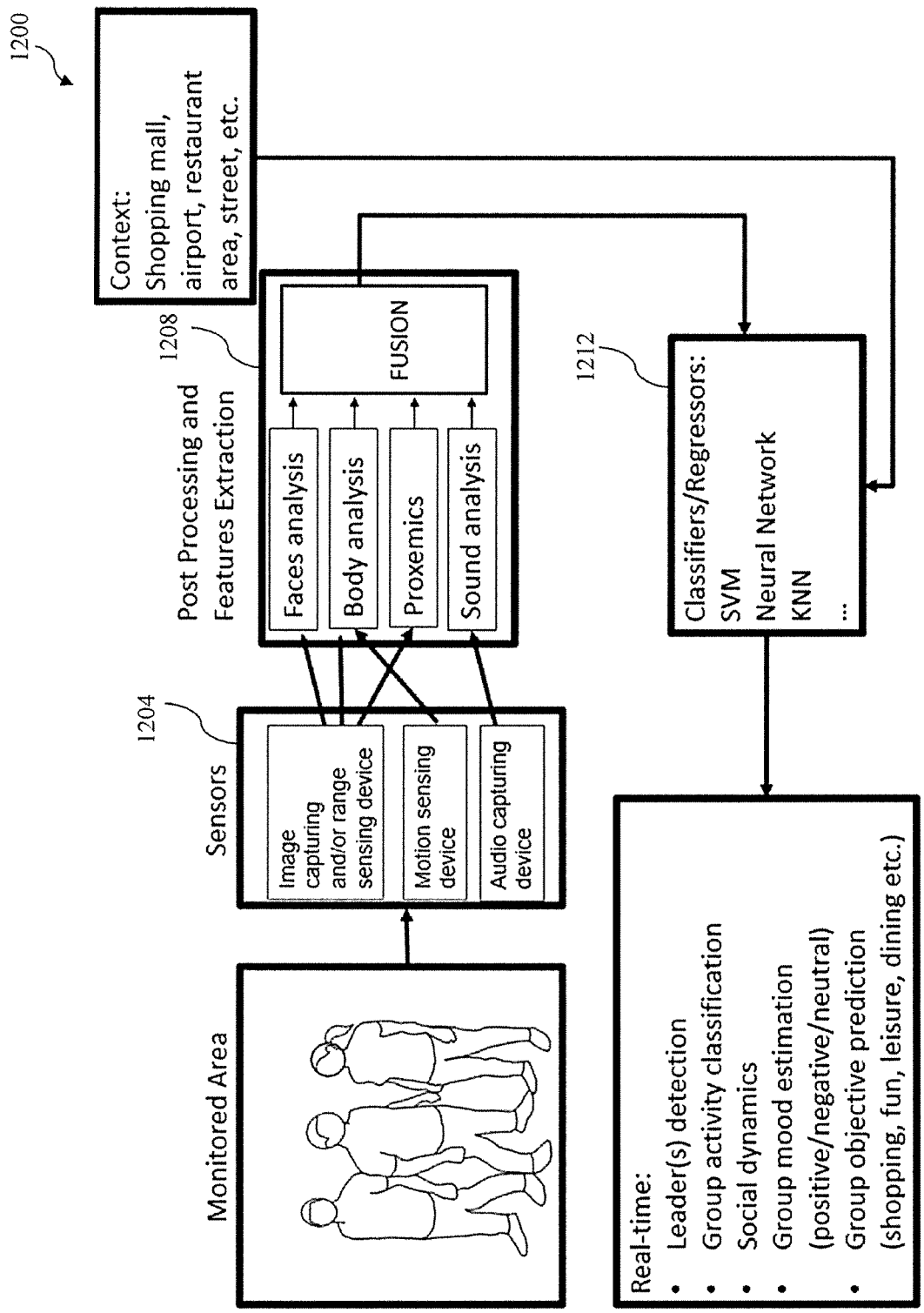
FIG. 12 depicts a block diagram illustrating an example system for generating an output with respect to a group of individuals according to various example embodiments of the present invention.

FIG. 12 depicts a block diagram illustrating an example system 1200 for generating an output with respect to a group of individuals according to various example embodiments of the present invention. As shown, the example system 1200 comprises a plurality of sensors 1204 arranged for obtaining sensing data with respect to the plurality of individuals in an area being monitored, a plurality of types of classifiers or analysis modules 1208, each for determining the corresponding type of features of each individual in the group (individual-based features) and/or the corresponding type of features associated with the group (group-based features), and a group characteristic classifier or analysis module 1212 configured to generate a classification result/output corresponding to the group characteristic information based on a fusion or combination of the different types of features determined. As shown in FIG. 12, for example, the plurality of types of classifiers or analysis modules 1208 may include a facial feature classifier configured to determine one or more facial features based on the sensing data (e.g., image data) obtained from an image capturing device (e.g., camera), a body feature classifier configured to determine one or more body features based on the sensing data (e.g., image data and motion data) obtained from the image capturing device and a motion sensing device (e.g., MICROSOFT KINECT or the like), a proxemics-based feature classifier configured to determine one or more proxemics-based feature associated with the group based on the sensing data (e.g., image data) obtained from the image capturing device, and a speech feature classifier configured to determine one or more speech features based the sensing data obtained from an audio capturing device (e.g., microphone). As also shown in FIG. 12, for example, the group characteristic classifier 1212 may be based on SMV, PNN, or KNN, or a combination thereof. By way of example only and without limitation, the group characteristic information determined by the group characteristic classifier 1212 may include one or more of group relationship information (e.g., family, couple, colleagues, and so on), group leader information, a group activity information, social dynamics information, group mood information (e.g., positive, negative or neutral) and group objective information (e.g., shopping, leisure, dining, and so on).

Accordingly, various embodiments of the present invention are advantageously able to generate an output (group characteristic information) with respect to the group of individuals identified (i.e., at a group level). Therefore, various embodiments of the present invention are advantageously able to understand group dynamics/characteristics and enables the provision of information that effectively targets a group of individuals. For example, examples types of group characteristic information may include one or more of relationship or context of the group (e.g., couple, colleagues, father-child, friends, and so on), leader of the group (e.g., the influencer), and activity of the group (e.g., shopping, eating, travelling, and so on). As a result, it is possible to determine appropriate content (e.g., better suited content that is more relevant to the group) to the group based on the relationship or context of the group determined.

As mentioned hereinbefore, the method and system described herein according to various embodiments of the present invention may be applied in a wide variety of applications. For example, possible types of applications may include targeted advertisement content (e.g., identify a group of tourist (including identifying the group leader based on various factors, such as holding a flag), and creating targeted advertisement content for the group, e.g., based on the language spoken, age, gender, and so on of the majority of the individuals in the group), targeted security alert (e.g., scanning groups of people in crowded places, such as trains, airports, and malls, bullying at school, and so on), entertainment (e.g., adaptive gaming in amusement parks), sports (e.g., predict outcome in a game based on players' dynamics), social robotics and computational attention, home electronics (e.g., smart televisions configured to recommend a program for a group of individuals), team management (e.g., detect tensions among team members (e.g., employees) such that appropriate actions may be taken to remedy the issue) and so on.

While embodiments of the invention have been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:

1. A computer-implemented method for generating an output with respect to a group of individuals, the method comprising:
    identifying the group of individuals amongst a plurality of individuals in an area being monitored by one or more sensors using a schematic model,
    wherein the schematic model is composed of at least one of a skeleton model and a face model which determines a separation, and an orientation of each individual of said plurality of individuals and whether to assign an adjacent pair of individuals as belonging to the group of individuals based on the separation determined with respect to the adjacent pair of individuals and the orientation determined with respect to each individual of the adjacent pair of individuals,
    wherein said separation is determined based on one or more predetermined first portions of the respective skeleton model or the face model and said orientation is determined based on a direction vector generated based on one or more predetermined second portions of the respective skeleton model or the face model;
    determining a group characteristic information associated with the group of individuals based on one or more individual-based features determined for each individual in the group; and
    generating the output based on the group characteristic information determined for the group of individuals.

2. The method according to claim 1, further comprising determining one or more group-based features associated with the group of individuals based on the one or more individual-based features determined for each individual in the group, wherein the group characteristic information is determined based on the one or more group-based features determined for the group of individuals.

3. The method according to claim 1, wherein said determining whether to assign the adjacent pair of individuals comprises determining to assign the adjacent pair of individuals as belonging to the group on individuals if the separation between the adjacent pair of individuals determined satisfies a predetermined separation condition and the orientations of the adjacent pair of individuals determined satisfy a predetermined orientation condition.

4. The method according to claim 1, wherein the group characteristic information is a group relationship information indicating a relationship amongst the individuals in the group.

5. The method according to claim 1, wherein the output is selected from the group consisting of a targeted advertisement content, a targeted security alert, an environment setting, and a signal comprising the group characteristic information.

6. The method according to claim 1, wherein the one or more sensors are selected from the group consisting of a motion sensing device, a range sensing device, an image capturing device, and an audio capturing device.

7. The method according to claim 6, wherein the one or more individual-based features determined are selected from the group consisting of a facial feature, a body feature, aspatial feature, and a speech feature.

8. The method according to claim 7, wherein said determining one or more individual-based features comprises determining each of the facial feature, the body feature, the spatial feature, and the speech feature for each individual in the group of individuals, and said determining a group characteristic information comprises determining the group characteristic information based on each of the facial feature, the body feature, the spatial feature, and the speech feature associated with each individual in the group of individuals.

9. A computer-implemented method for generating an output with respect to a group of individuals, the method comprising:
    identifying the group of individuals amongst a plurality of individuals in an area being monitored by one or more sensors using a schematic model,
    wherein the schematic model is composed of at least one of a skeleton model and a face model which determines a separation, and an orientation of each individual of said plurality of individuals, and whether to assign an adjacent pair of individuals as belonging to the group of individuals based on the separation determined with respect to the adjacent pair of individuals and the orientation determined with respect to each individual of the adjacent pair of individuals,
    wherein said determining whether to assign an adjacent pair of individuals comprises determining to assign the adjacent pair of individuals as belonging to the group on individuals,
    if the separation between the adjacent pair of individuals determined satisfies a predetermined separation condition and the orientations of the adjacent pair of individuals determined satisfy a predetermined orientation condition,
    wherein the predetermined separation condition is that the separation determined is less than a predetermined separation, and the predetermined orientation condition is that the orientations determined are toward each other;
    determining a group characteristic information associated with the group of individuals based on one or more individual-based features determined for each individual in the group; and
    generating the output based on the group characteristic information determined for the group of individuals.

10. The method according to claim 9, wherein the group characteristic information is a group relationship information indicating a relationship amongst the individuals in the group.

11. The method according to claim 9, wherein the output is selected from the group consisting of a targeted advertisement content, a targeted security alert, an environment setting, and a signal comprising the group characteristic information.

12. The method according to claim 9, wherein the one or more sensors are selected from the group consisting of a motion sensing device, a range sensing device, an image capturing device, and an audio capturing device.

13. The method according to claim 12, wherein the one or more individual-based features determined are selected from the group consisting of a facial feature, a body feature, a spatial feature, and a speech feature.

14. The method according to claim 13, wherein said determining one or more individual-based features comprises determining each of the facial feature, the body feature, the spatial feature, and the speech feature for each individual in the group of individuals, and said determining a group characteristic information comprises determining the group characteristic information based on each of the facial feature, the body feature, the spatial feature, and the speech feature associated with each individual in the group of individuals.

15. A system for generating an output with respect to a group of individuals, the system comprising:
a memory;
at least one processor communicatively coupled to the memory and configured to:
identify the group of individuals amongst a plurality of individuals in an area being monitored by one or more sensors using a schematic model wherein the schematic model is composed of at least one of a skeleton model and a face model which determines a separation, an orientation of each individual of said plurality of individuals and whether to assign an adjacent pair of individuals as belonging to the group of individuals based on the separation determined with respect to the adjacent pair of individuals and the orientation determined with respect to each individual of the adjacent pair of individuals,
wherein said separation is determined based on one or more predetermined first portions of the respective skeleton model or the face model and said orientation is determined based on a direction vector generated based on one or more predetermined second portions of the respective skeleton model or the face model;
determine a group characteristic information associated with the group of individuals based on one or more individual-based features determined for each individual in the group; and
generate the output based on the group characteristic information determined for the group of individuals.

16. The system according to claim 15, wherein the at least one processor is further configured to determine one or more group-based features associated with the group of individuals based on the one or more individual-based features determined for each individual in the group, wherein the group characteristic information is determined based on the one or more group-based features determined for the group of individuals.

17. The system according to claim 15, wherein the output is selected from the group consisting of a targeted advertisement content, a targeted security alert, an environment setting, and a signal comprising the group characteristic information.

18. The system according to claim 15, further comprising the one or more sensors, wherein the one or more sensors are selected from the group consisting of a motion sensing device, a range sensing device, an image capturing device, and an audio capturing device.

19. The system according to claim 18, wherein the one or more individual-based features determined are selected from the group consisting of a facial feature, a body feature, a spatial feature, and a speech feature.

20. The system according to claim 19, wherein said determine one or more individual-based features comprises determining each of the facial feature, the body feature, the spatial feature, and the speech feature for each individual in the group of individuals, and said determine a group characteristic information comprises determining the group characteristic information based on each of the facial feature, the body feature, the spatial feature, and the speech feature associated with each individual in the group of individuals.

21. A system for generating an output with respect to a group of individuals, the system comprising:
a memory;
at least one processor communicatively coupled to the memory and configured to:
identify the group of individuals amongst a plurality of individuals in an area being monitored by one or more sensors using a schematic model;
wherein the schematic model is composed of at least one of a skeleton model and a face model which determines a separation, an orientation of each individual of said plurality of individuals and whether to assign an adjacent pair of individuals as belonging to the group of individuals based on the separation determined with respect to the adjacent pair of individuals and the orientation determined with respect to each individual of the adjacent pair of individuals;
wherein said determining whether to assign an adjacent pair of individuals comprises determining to assign the adjacent pair of individuals as belonging to the group on individuals
if the separation between the adjacent pair of individuals determined satisfies a predetermined separation condition and the orientations of the adjacent pair of individuals determined satisfy a predetermined orientation condition;
wherein the predetermined separation condition is that the separation determined is less than a predetermined separation and the predetermined orientation condition is that the orientations determined are toward each other;
determine a group characteristic information associated with the group of individuals based on one or more individual-based features determined for each individual in the group; and
generate the output based on the group characteristic information determined for the group of individuals.

22. The method according to claim 21, wherein the group characteristic information is a group relationship information indicating a relationship amongst the individuals in the group.

23. The method according to claim 21, wherein the output is selected from the group consisting of a targeted advertisement content, a targeted security alert, an environment setting, and a signal comprising the group characteristic information.

24. The method according to claim 21, wherein the one or more sensors are selected from the group consisting of a motion sensing device, a range sensing device, an image capturing device, and an audio capturing device.

25. The method according to claim 24, wherein the one or more individual-based features determined are selected from the group consisting of a facial feature, a body feature, a spatial feature, and a speech feature.

26. The method according to claim 25, wherein said determining one or more individual-based features comprises determining each of the facial feature, the body feature, the spatial feature, and the speech feature for each individual in the group of individuals, and said determining a group characteristic information comprises determining the group characteristic information based on each of the facial feature, the body feature, the spatial feature, and the speech feature associated with each individual in the group of individuals.

* * * * *